(12) United States Patent
Paul et al.

(10) Patent No.: US 7,642,225 B2
(45) Date of Patent: Jan. 5, 2010

(54) DETERGENT COMPOSITION CONTAINING A CATIONISED SILICONE DELIVERY SYSTEM

(75) Inventors: Sudipto Kumar Paul, Mumbai (IN); Kizhakera Nairveetil Ramachandran, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 766 days.

(21) Appl. No.: 10/543,473

(22) PCT Filed: Jan. 23, 2004

(86) PCT No.: PCT/EP2004/000662

§ 371 (c)(1), (2), (4) Date: Jun. 19, 2006

(87) PCT Pub. No.: WO2004/066972

PCT Pub. Date: Aug. 12, 2004

(65) Prior Publication Data

US 2006/0269505 A1    Nov. 30, 2006

(30) Foreign Application Priority Data

| Jan. 29, 2003 | (IN) | ............... 108MUM2003 |
| Jan. 29, 2003 | (IN) | ............... 109MUM2003 |
| Apr. 22, 2003 | (GB) | ............... 0309017.2 |
| May 12, 2003 | (GB) | ............... 0310786.9 |

(51) Int. Cl.
C11D 1/02 (2006.01)
C11D 3/37 (2006.01)
C11D 9/00 (2006.01)

(52) U.S. Cl. .............. 510/122; 510/123; 510/443; 510/446; 510/466; 510/504; 424/401; 424/498; 424/70.12

(58) Field of Classification Search .......... 510/122, 510/123, 443, 446, 466, 504; 424/401, 498, 424/70.12
See application file for complete search history.

(56) References Cited

U.S. PATENT DOCUMENTS

| 4,673,568 A | 6/1987 | Grollier et al. |
| 4,710,314 A | 12/1987 | Madrange et al. |
| 5,154,849 A | 10/1992 | Visscher et al. |
| 5,362,484 A | 11/1994 | Wood et al. |
| 5,661,120 A | 8/1997 | Finucane et al. |
| 5,981,465 A | 11/1999 | Ramachandran et al. |
| 6,136,304 A | 10/2000 | Pyles |
| 2001/0031270 A1 | 10/2001 | Douin et al. |
| 2002/0071819 A1* | 6/2002 | Giles et al. ............ 424/70.21 |
| 2002/0082174 A1 | 6/2002 | Aldrich et al. |

FOREIGN PATENT DOCUMENTS

| DE | 102 14 290 | 10/2003 |
| EP | 0 150 872 | 1/1985 |
| EP | 1 396 535 | 9/2002 |
| GB | 2 161 172 | 7/1984 |
| WO | 97/04743 | 2/1997 |
| WO | 02/03936 | 1/2002 |
| WO | 02/092052 | 11/2002 |
| WO | 03/035765 | 5/2003 |
| WO | 2004/010967 | 2/2004 |
| WO | 2004/032887 | 4/2004 |

OTHER PUBLICATIONS

*International Search Report*, PCT/EP2004/000662, mailed Jul. 16, 2004, 3 pp.
GB Search Report, GB 0319786.9, dated Sep. 26, 2003—1 p.
Mitsubishi Chem. Corp., JP 2004 043368, Feb. 12, 2004, Chemical Abstracts Service, Columbus, Ohio, XP002282500, Database Accession No. 140: 186961, abstract.
F. Muller, et al., "divergent surfactant systems for household produts", World Conference on Detergents, 5th, Montreux, Oct. 13-17, 2002, 2003, pp. 208-211, XP 008031088.

* cited by examiner

*Primary Examiner*—Brian P Mruk
(74) *Attorney, Agent, or Firm*—Alan A. Bornstein

(57) ABSTRACT

A cleansing cosmetic composition comprising; i) a cationized silicon delivery system selected from one or more of a) a cationized fatty alkyl silicone copolymer; b) a cationized dimethiconol complex and c) a cationized high viscosity lower alkyl silicone fluid with or without cationized silicone gum blend; and ii) detergent active. Also disclosed is a cationized silicone delivery system comprising: a) 15-50 parts of a cationized fatty alkyl silicone copolymer; b) 5-50 parts of a cationized dimethiconol complex; and c) 1-50 parts of a cationized high viscosity lower alkyl silicone fluid with cationized silicone gum blend.

28 Claims, No Drawings

DETERGENT COMPOSITION CONTAINING A CATIONISED SILICONE DELIVERY SYSTEM

The present invention relates to a cosmetic composition suitable for delivering superior conditioning benefits on substrates such as hair, skin and the like by the enhanced deposition of benefit agents, in particular silicones to substrates such as hair, skin and the like. The cosmetic composition can be provided in variety of formulations, in particular, rinse-off cleansing or care formulations for cosmetic applications. The composition provides superior conditioning while delivering excellent cleansing. The invention also relates to method for superior conditioning of substrates such as skin, hair and the like using the cosmetic composition of the invention.

In a further embodiment, the present invention also relates to a cationised silicone composition, and in particular to a cationised silicon system/composition suitable for deposition of desired amounts of silicones as benefit agents on substrates such as hair, skin and the like from a variety of formulations, in particular rinse-off cleansing and/or care formulations for cosmetic applications.

Silicones are known to provide a light, silky feel on hair and skin. Their effectiveness is dependent on the extent of deposition. However, for cleansing products, since the surfactants present are engaged in the removal of oil from the substrate, mere addition of silicone(s) oil into the composition does not serve any purpose, as they tend to get washed off. The art talks about various methods to increase deposition of silicones from the cosmetic cleansing compositions. The routes referred to include using blends of silicones and/or modified silicones, cationic polymers as deposition aids and special surfactant systems.

In particular, when silicones are incorporated in bar soaps at very low dosages, they have a tendency to wash off along with the soap, leaving no silicone residue on the skin and hair. When silicones are added to bar soaps in the form of fluids, they tend to become emulsified and the emulsion is washed away and shows no substantivity to skin and hair. Therefore, even very viscous fluids fail to provide the sensory benefits of silicones when applied through bar soaps. Compositions containing silicones also tend to show reduced lather formation.

With regard to the prior art, U.S. Pat. No. 4,70,314 teaches an aqueous composition, stable on storage, comprising soap, silicone cationic polymer, cationic surfactant and cationic polymer. The cationic silicone polymer referred to is limited to the class of amodimethicones which has been specifically proposed to achieve the desired storage stability of anioinic surfactants with cationic compounds, and does not deal with desired deposition levels of silicones on substrates.

U.S. Pat. No. 5,154,849 disclosed the possible use of silicone component consisting essentially of a mixture of silicon gum and silicone fluid to achieve durable skin conditioning, superior smooth and soft skin feel, lather and improved rinsing. In particular, it discloses a mild skin cleansing composition in the form of a bar comprising from about 0.5% to about 20% of a mixture of a silicone gum and a silicone fluid wherein the gum:fluid ratio is from about 10:1 to about 1:10, preferably from about 4:1 to about 1:4, most preferably from about 3:2 to about 2:3. The silicone component is a skin mildness/moisturising aid which imparts superior, durable conditioning to skin washed with the composition. Processes for preparing a mild skin cleansing toilet bar with this silicone component are disclosed. While this prior art also makes use of silicone compounds for mild skin cleansing, the same does not specifically traverse the need for improving the level of silicone deposition and related benefits.

U.S. Pat. No. 5,981,465 teaches a method for increasing surface deposition of silicone from soap and improving processing characteristics of soap, and corresponding compositions are disclosed. The compositions include a fatty alkyl silicone, a fatty silicate ester, a high viscosity lower alkyl silicone fluid, a silicone surfactant, and an organic surfactant. The organic surfactant is one or more of a nonionic, cationic or anionic surfactants.

U.S. Pat. No. 5,661,120 describes detergent bar compositions comprising liquid silicone compounds or emulsions of said compounds which are used in relatively small levels as processing aids. These compounds allow pellets coming off a chill roll or refiner to be less tacky, such that they do not readily clog machinery when the pellets are transferred to silos.

US 2002/0082174 A1 also talks about achieving efficient deposition of cosmetically active ingredients onto skin or hair, and discloses a cleansing cosmetic composition containing a anionic, cationic, amphoteric surfactants or mixtures thereof, with an alkoxylated nonionic surfactant as co-surfactant, a water insoluble component and a cationic conditioning polymer. While the composition is stated to deliver improved silicone deposition, good cleansing and conditioning, it is however limited to systems with a maximum surfactant content or the detergent active content of 60%, which is a mix of surfactants and co-surfactants.

It is also known to use phase transfer catalyst and quaternizing agents to achieve cationisation of organic polymers and their complexes. Cationised amodimethicone is described in the art. Cationised complexes offer superior substantivity to biological surfaces.

It would be apparent from the above that while it is well known that silicones constitute active benefit ingredients for various cosmetic formulations, it's selection and form of incorporation in various cosmetic formulations is important to achieve the desired stability, compatibility with various other ingredients, and importantly, the effective deposition of the silicones onto said substrates as benefit agents.

As would be apparent from the above state of the art, surfactants constitute the basic constituent of a cleansing composition, and cleansing and/or cosmetic formulations incorporating silicones as benefit agents need to be compatible with various surfactant systems for effective and wide application or use of silicones as benefit agents in cosmetic formulations. Moreover, considering that compositions with higher detergent active compositions are common, it is also important to be able to achieve superior silicone deposition and hence conditioning from such compositions without any limitation in levels of active detergent in such formulations.

In addition, considering that silicones are well known to impart desired sensory/cosmetic benefit on deposition on substrates such as skin, hair and the like, there has been a constant need in the art to provide for effective silicone delivery systems which could provide for the desired delivery of the silicones on substrates such as from rinseoff formulations and the like. However it has been found that the form of the silicone and its compatibility with the formulation where it is desired to be incorporated is important, and it has been extremely difficult to provide for silicones which could be easily incorporated in any variety of formulations for effective delivery on biological substrates. It is typically found that presently available silicones either are difficult to incorporate in a soap bar because of their high viscosity, or when incorporated the composition does not offer perceivable benefits.

It thus has been the basic advantage of the invention to be able to provide for a wide range of cleansing cosmetic compositions, with selective cationised silicone active which would serve for effective delivery of the silicones as the benefit agent onto substrates such as hair, skin and the like.

Another advantage of the present invention is directed to being able to provide a wide range of synergistic cleansing cosmetic formulations comprising selective cationised silicone actives which would serve for enhanced delivery of the silicones as the benefit agent onto substrates such as hair, skin and the like.

Yet further advantage of the present invention is directed to being able to provide selective cationised silicone delivery systems which may be used in cleansing cosmetic compositions which may be stable and compatible with any variety of conventional surfactant systems, and achieve desired delivery and retention of silicone benefit agent on any biological substrate even as a rinse-off product.

Yet another advantage of the present invention is directed to being able to provide cleansing cosmetic compositions comprising selective cationised silicone delivery systems which would be stable and compatible with any variety of conventional surfactant systems, and achieve desired delivery and retention of silicone benefit agent on any biological substrate to achieve superior conditioning without any limitations in level of detergent active.

Yet another advantage of the present invention is directed to being able to provide an improved method of treating substrates such as hair, skin and the like whereby it would be possible to achieve effective deposition of silicone benefit agent onto such substrates even by applying rinse-off formulations.

Yet another advantage of the present invention is being able to provide for a silicone delivery system suitable for incorporation in a wide range of cosmetic or other rinseoff formulations which would serve for effective delivery of the silicone(s) for desired benefit attributes.

Yet another advantage of the present invention is to be able to provide for cationised silicones and/or cationised silicone delivery systems which would provide the desired flexibility to incorporate cationic silicones, either as such or through dispersions or emulsions using nonionic, cationic and anionic surfactants in bar soap formulations.

Yet a further advantage of the present invention is directed to being able to provide cationised silicones and/or cationised silicone delivery systems which can be used as such, or as an emulsion or dispersion and added to soap noodles or converted to a granular additive with conventional fillers and added directly to soap.

Thus according to the present invention, in a first aspect there is provided a cleansing cosmetic composition comprising: (i) a selective cationised silicone delivery system selected from one or more of (a) a cationised fatty alkyl silicone copolymer; (b) cationised dimethiconol complex and (c) cationised high viscosity lower alkyl silicone fluid with or without cationised silicone gum blend, (ii) detergent active, and optionally (iii) cationic polymer.

In a further particularly preferred aspect of the invention, there is provided a cationised silicone delivery system comprising a cationised silicone active selected from one or more of (a) a cationised fatty alkyl silicone copolymer; (b) cationised dimethiconol complex and (c) cationised high viscosity lower alkyl silicone fluid with or without cationised silicone gum blend.

In accordance with a preferred aspect of the cationised silicone delivery system, this may comprise a selective synergistic blend of (a) 15-50 parts of a cationised fatty alkyl silicone copolymer; (b) 5-50 cationised dimethiconol complex, and (c) 1-50 parts of a cationised high viscosity lower alkyl silicone fluid and cationised silicone gum blend. In a preferred embodiment, the cationised silicone delivery system further comprises 2 to 10 parts of an organic surfactant.

In accordance with another preferred aspect the cationised silicone delivery system may comprise a selective synergistic blend of (a) 15-50 parts of a cationised fatty alkyl silicone copolymer; (b) 5-50 cationised dimethiconol complex and (c) 1-50 parts of a cationised high viscosity lower alkyl silicone fluid and cationised silicone gum blend, and (d) 2-10 parts of an organic surfactant.

In the above disclosed cationised silicone delivery system, for the cationised fatty alkyl silicone copolymer, alkyl is defined as a branched or straight alkyl chain containing 10 to 80 carbon atoms, and fatty is defined as a fatty acid with a straight chain containing 10 to 30 carbon atoms. The viscosity range of the fatty alkyl silicone copolymer is $0.5 \times 10^5$ to $5 \times 10^6$ cp (centipoise), with all viscosity measurements (unless otherwise stated) being at 25° C. A preferred alkyl chain contains 60 carbon atoms and the preferred fatty acid contains 16 to 18 carbon atoms. The preferred viscosity range for the polymer is $1 \times 10^5$ to $1 \times 10^6$ cp.

The cationised dimethiconol complex has a viscosity range from $1 \times 10^6$ to $50 \times 10^6$ cp and preferably $10 \times 10^6$ to $20 \times 10^6$ cp.

The cationised high viscosity lower alkyl silicone fluid has a viscosity range of $0.5 \times 10^6$-$600 \times 10^6$ cp. The blend of fluid to gum is x: 1, with x varying from 0.1 to 20 and preferably 1.

Advantageously, in one aspect the selective cationised silicone delivery system can combine with a variety of surfactant systems to provide for a wide range of cosmetic formulations with desired silicone deposition on substrates. The surfactant (which is preferable organic) can be selected to be any conventional surfactant system, and can typically be a nonionic, cationic or anionic surfactant. Importantly, in some aspects the cosmetic composition of the invention can have detergent active even at levels higher than 60% by wt., and yet achieve both the desired silicone deposition on substrate and better cleansing properties.

In accordance with a further aspect the cleansing cosmetic composition comprises (i) 0.1% to 20%, preferably 0.5% to 16%, more preferably 1% to 5% by wt. of a selective cationised silicone delivery system selected from one or more of (a) a cationised fatty alkyl silicone copolymer; (b) cationised dimethiconol complex and (c) cationised high viscosity lower alkyl silicone fluid with or without cationised silicone gum blend (ii) 20% to 85%, preferably 30% to 80%, more preferably 40% to 70% by wt. detergent active, and optionally (iii) 0.001% to 10%, preferably 0.01% to 1%, more preferably 0.05% to 0.5% by wt. cationic polymer.

A preferred aspect of one facet of the invention is directed to a cleansing cosmetic composition comprising: (i) a cationised silicone delivery system comprising a cationised silicone active selected from one or more of (a) a cationised fatty alkyl silicone copolymer; (b) cationised dimethiconol complex; and (c) cationised high viscosity lower alkyl silicone fluid with or without cationised silicone gum blend; (ii) anionic detergent active and (iii) a cationic polymer.

A further preferred aspect of the invention is directed to a cleansing cosmetic composition comprising (i) a cationised silicone delivery system comprising a cationised silicone active selected from one or more of (a) a cationised fatty alkyl silicone copolymer; (b) cationised dimethiconol complex; and (c) cationised high viscosity lower alkyl silicone fluid with or without cationised silicone gum blend; (ii) soap (which may be an alkali metal salt of a carboxylic fatty acid) and (iii) a cationic polymer.

Yet another preferred aspect of the invention provides a cleansing cosmetic composition comprising (i) a cationised silicone delivery system comprising a cationised silicone active selected from one or more of (a) a cationised fatty alkyl silicone copolymer; (b) cationised dimethiconol complex; (c) cationised high viscosity lower alkyl silicone fluid with or without cationised silicone gum blend; and (d) an organic surfactant; (ii) detergent active and (iii) a cationic polymer.

In accordance with yet further preferred aspect of the invention the cleansing composition comprises a cationised silicone delivery system comprising a selective synergistic blend of said (a) a cationised fatty alkyl silicone copolymer (b) cationised dimethiconol complex and (c) a cationised high viscosity lower alkyl silicone fluid and cationised silicone gum blend and (d) an organic surfactant.

In accordance with a preferred aspect, the cleansing composition comprises (i) a selective synergistic blend of cationised silicone delivery system comprising (a) 15-50 parts of a cationised fatty alkyl silicone copolymer; (b) 5-50 cationised dimethiconol complex; (c) 1-50 parts of a cationised high viscosity lower alkyl silicone fluid and cationised silicone gum blend; and (d) an organic surfactant (ii) detergent active and (iii) a cationic polymer.

In accordance with yet further aspect of the present invention, there is provided a synergistic cleansing cosmetic composition comprising (i) a cationised silicone delivery system comprising a selective synergistic blend of said (a) a cationised fatty alkyl silicone copolymer; (b) cationised dimethiconol complex and (c) a cationised high viscosity lower alkyl silicone fluid and cationised silicone gum blend; and (d) an organic surfactant (ii) detergent active and (iii) cationic polymer.

In further preferred aspects, there is provided a process for producing the cationised silicone system of the invention, comprising providing the aid cationised silicone actives selected from one or more of (a) a cationised fatty alkyl silicone copolymer; (b) cationised dimethiconol complex and (c) cationised a high viscosity lower alkyl silicone fluid with or without cationised silicone gum blend following a conventional cationizing process. The cationisation process is described hereafter.

Preferably, in the cosmetic formulation of the invention the detergent active is an anionic surfactant, specifically a soap and more specifically an alkali metal salt of a carboxylic fatty acid.

According to a further aspect the present invention provides an improved method of cosmetically treating substrates such as skin, hair and the like comprising contacting the substrate to be treated with said cleansing cosmetic composition of the invention discussed above.

The invention thus provides for cleansing cosmetic compositions and delivery systems which can improve the deposition of silicone on the skin and hair as detailed above.

As stated above the composition comprises a selective cationised silicone delivery system selected from a cationic fatty alkyl silicone copolymer, cationised dimethiconol, a cationic high viscosity fluid silicone with or without cationised silicone gum blend and optionally (though in some instances preferably) organic surfactants.

In accordance with an aspect of the present invention, the cosmetic compositions of the present invention contain a synergistic blend of fatty alkyl cationised silicone copolymer, cationic high viscosity silicone fluid and cationised dimethiconol. A fatty alkyl silicone useful for the present invention is a copolymer of stearic acid and cetearyl methicone. The cationised fatty alkyl silicone copolymer may comprise 10-30 parts by weight per 100 parts of a soap additive composition, and preferably, about 20 parts; the cationised dimethiconol may also comprise 5-30 parts by weight per 100 parts of a soap additive composition, and preferably, about 25 parts.

The cationised high viscosity fluid silicone is present at a level which is effective to deliver a skin sensory benefit, for example, from 1-50 parts by weight, and preferably from 10-30 parts by weight per 100 parts of a soap additive composition. High viscosity fluid silicone, as used herein, denotes a silicone with viscosity ranging from about $0.5 \times 10^6$ to $600 \times 10^6$ cp. Silicone fluids useful in the present invention may be polyalkyl siloxanes, polyaryl siloxanes, or polyalkylaryl siloxanes of suitable viscosity and molecular weight. The polyalkyl siloxanes that may be used herein include, for example, polydimethyl siloxanes.

In a preferred cationisation process, in a 1500 ml reactor, 1000 g of silicone fluid (mix of cationised fatty alkyl silicone copolymer, cationised dimethiconol complex and cationised a high viscosity lower alkyl silicone fluid with or without cationised silicone gum blend, in the required ratios) and 100 g of iso-propyl alcohol are thoroughly mixed using mechanical stirrer. The process is conducted in an inert atmosphere with nitrogen blanketing. After heating to 70° C., 10 g quaternizing catalyst and 10 g dimethylsulphate mixture are added. The reactor is maintained at 70° C. for 4 hrs under nitrogen atmosphere. After the reaction the material was vacuum distilled to remove the iso-propyl alcohol. The polymer was washed with water and dried under vacuum for several hours.

The quaternizing catalyst can be drawn from a group of the following.

tetramethyl ammonium hydroxide
trimethyl N-propyl hydroxide
trimethyl N-2 pentyl hydroxide The composition may additionally preferably contain mixture of 1:1 quaternary catalyst and dimethylsulphate, which is present at a level of 0.01% to 5% and preferably at 0.5% to 1% level.

In another aspect, the invention relates to a method for increasing surface deposition of the cationised silicone on any biological substrate comprising applying to said substrate a formulation comprising the cationised silicone delivery system as such, or through dispersions or emulsions or combinations thereof.

It is thus possible by way of the present invention to provide for an improved cationised silicone delivery system which could synergistically improve the delivery of the desired silicone active on any biological substrate, including from rinse-off formulations. The synergistic silicone delivery system of the invention involving the blend of (a) a cationised fatty alkyl silicone copolymer; (b) cationised dimethiconol complex and (c) a cationised high viscosity lower alkyl silicone fluid with or without silicone gum blend is found to be especially suitable for hair care and bar soap applications, including the rinseoff forms thereof.

The organic surfactants useful herein may be selected from a wide range of surfactants including from the group of cationic, anionic, and nonionic surfactants suitable for personal products. These components are generally present from about 1-10 parts per 100 parts of the additive composition, preferably from about 4 parts to 6 parts. Preferred anionic surfactants for use in the present compositions are sodium laureth-7 sulfate and diethylene glycol monooleate. Suitable cationic surfactants which may be used are dicocodimethylammonium chloride and N-(3-chloroallyl) hexaminium chloride. Suitable nonionic surfactants which may be used in the invention are the lauryl ether polyoxyethylenes, and higher and lower molecular weight versions.

The cleansing compositions according to the invention will preferably comprise detergent actives that may be soap or non-soap surfactants, and generally chosen from anionic, nonionic, cationic, zwitterionic detergent actives or mixtures thereof. Suitable examples of detergent-active compounds are compounds commonly used as surface-active agents given in the well-known textbooks "Surface Active Agents", Volume I by Schwartz and Perry and "Surface Active Agents and Detergents", Volume II by Schwartz, Perry and Berch or "Handbook of Surfactants", M. R. Porter, Blackie Publishers, 1991.

Non-limiting, cationic polymers that can be used in compositions of the invention include cationic cellulose derivatives, cationic starches, copolymers of a dialkyl quaternary ammonium salt and acrylamide, quaternized polyvinylpyrrolidone, quaternized vinylpyrrolidone vinylimidazol polymers, polyglycol amide condensates, quaternized collagen polypeptide, polyethylene amine, cationised silicon polymer, cationic silicone polymers, copolymers of adipic acid and dimethylamino-hydroxypropyl diethylene triamine, polyaminopolyamide and their water soluble crosslinked polymers, cationic chitin derivatives and cationic guargums. A preferred cationic conditioning polymer is a cationic derivative of guar gum. The most preferred cationic polymer is guar hydroxy propyl trimethyl ammonium chloride.

The present compositions may optionally include soap filler such as talc. Any of the standard fillers which are used in the manufacture of soap bars may be used. Filler may be included in the present compositions at levels from about 100-1000 parts by weight per 100 parts soap additive composition, and preferably 200-600 parts.

The details of the invention its objects and advantages are further explained hereunder in greater detail in relation to the following non-limiting exemplary illustrations.

EXAMPLES

Hair Care Formulations

The hair care formulation was formulated as a bar and was obtained by mixing the ingredients and extruding the formulation as shown in Table 1 for the different examples. The silicone blend comprised of 1:1:1:1 of (a) cationised fatty alkyl silicon copolymer (b) cationised dimethiconol complex (c) cationised high viscosity lower alkyl silicone fluid (d) cationised silicone gum blend. The conventional silicone was procured from GE.

TABLE 1

| Composition (% wt.) | Example A | Example B | Example C |
|---|---|---|---|
| Soap | 62 | 80 | 62 |
| Silicone blend | — | — | 1.5 |
| Silicone Conventional | 1.5 | — | — |
| Cationic polymer | — | — | 0.1 |
| Electrolyte | 1 | 1 | 1 |
| Filler | 18 | 4 | 18 |
| Water | To 100 | To 100 | To 100 |

The silicone deposition achieved from the above formulations were tested following a standard protocol as described hereunder.

Method

Soap bars of different compositions as per Examples A, B and C were used. The bars were placed with consumers who used them in normal in-use conditions for a period of 7 days. They were then asked to rate the specific composition placed with them on a scale of 1 (very poor)-5 (excellent). The scores were collected and average for the entire sample. The score distributions were then subjected a statistical significance analysis as represented in Table 2 hereunder. The difference in the benefit between example A and example B (D1) was compared with the difference in benefit between example C and example 2 (D2). The ratio of D2 to D1 will give the relative benefit and a ratio>1 will demonstrate the superiority of the silicone blend according to the present invention.

TABLE 2

| Parameter | Ex. A | Ex. B | D1 | Ex. C | Ex. B | D2 | Ratio D2:D1 |
|---|---|---|---|---|---|---|---|
| Easy to comb | 4.76 | 4.65 | −0.11 | 4.4 | 4.1 | −0.3 | 2.7 |
| Tangle free and manageable | 4.65 | 4.63 | −0.02 | 4.63 | 4.43 | −0.2 | 10.0 |
| DN leave hair rough and dry | 4.64 | 4.57 | −0.07 | 4.8 | 4.3 | −0.5 | 7.1 |
| Makes hair soft | 4.75 | 4.7 | −0.05 | 4.74 | 4.52 | −0.22 | 4.4 |
| Makes hair shiny | 4.52 | 4.46 | −0.06 | 4.5 | 4.3 | −0.2 | 3.3 |

It would be well apparent from the above that the composition in accordance with the present invention incorporating the silicone delivery system a ratio>1, is achieved which indicated significantly superior conditioning from the formulation of Example C vis-à-vis the formulations of Examples A and B.

It is thus possible by way of the present invention to provide for a wide range of cleansing cosmetic compositions with selective cationised silicone actives which would serve for effective delivery of the silicones as the benefit agent onto substrates such as hair, skin and the like.

Importantly, the silicone delivery system used in the formulation of the invention provided synergistic cleansing cosmetic formulations with soap base which would serve for enhanced delivery of the silicones as the benefit agent onto substrates such as hair, skin and the like.

The composition of the invention is found to be stable and compatible with any variety of conventional surfactant system without limitations in the level of surfactant, and achieved desired delivery and retention of silicone benefit agent on any biological substrate even as a rinse-off product. The invention would also serve to provide improvement in method of treating substrates such as hair, skin and the like whereby it would be possible to achieve effective deposition of silicone benefit agent onto such substrates even by applying rinse-off formulations.

Examples 1 to 37

Exemplary compositions as detailed in Tables 3a and 3b were prepared by mixing the components in the order described. The mixing was achieved using a low rpm stirrer, and then inverted to emulsion using a colloid mill.

The organic surfactants used in examples were prepared as shown in Table 4.

The compositions of the examples in Table 3a and 3b were prepared by mixing the components as listed in the table, and then adding 1 gram of the composition to 100 grams soap noodles. The soap mixture was blended and made into soap bars.

TABLE 3a

|   | 1 | 2 | 3 | 4 | 5 | 6 | 7 | 8 | 9 | 10 | 11 | 12 | 13 | 14 | 15 | 16 | 17 | 18 |
|---|---|---|---|---|---|---|---|---|---|----|----|----|----|----|----|----|----|----|
| A1 | 62 | 62 | 62 | | | | | | | | | | | | | | | |
| A2 | | | | 62 | 62 | 62 | | | | | | | | | | | | |
| B1 | | | | | | | 62 | 62 | 62 | | | | | | | | | |
| B2 | | | | | | | | | | 62 | 62 | 62 | | | | | | |
| C1 | | | | | | | | | | | | | 62 | 62 | 62 | | | |
| C2 | | | | | | | | | | | | | | | | 62 | 62 | 62 |
| X | 8 | | | 8 | | | 8 | | | 8 | | | 8 | | | 8 | | |
| Y | | 8 | | | 8 | | | 8 | | | 8 | | | 8 | | | 8 | |
| Z | | | 8 | | | 8 | | | 8 | | | 8 | | | 8 | | | 8 |
| WATER | 30 | 30 | 30 | 30 | 30 | 30 | 30 | 30 | 30 | 30 | 30 | 30 | 30 | 30 | 30 | 30 | 30 | 30 |
| TOTAL | 100 | 100 | 100 | 100 | 100 | 100 | 100 | 100 | 100 | 100 | 100 | 100 | 100 | 100 | 100 | 100 | 100 | 100 |

X- Anionic surfactant system
Y- Cationic surfactant system
Z - Nonionic surfactant system A2, B2, C2, D2, E2, F2—Fluids corresponding to A1, B1, C1, D1, E1, F1 respectively, but each cationised.
A1, B1, C1, D1, E1, F1—Normal silicone fluids.
A1: High viscosity dimethicone
B1: Dimethiconol
C1: Fatty aklyl silicone copolymer
D1: High viscosity silicone gum
E1: 1:1:1 Blend of A1, B1, C1
F1: 1:1:1:1 Blend of A1, B1, C1, D1

TABLE 3b

|   | 19 | 20 | 21 | 22 | 23 | 24 | 25 | 26 | 27 | 28 | 29 | 30 | 31 | 32 | 33 | 34 | 35 | 36 | 37 |
|---|----|----|----|----|----|----|----|----|----|----|----|----|----|----|----|----|----|----|----|
| D1 | 62 | 62 | 62 | | | | | | | | | | | | | | | | |
| D2 | | | | 62 | 62 | 62 | | | | | | | | | | | | | |
| E1 | | | | | | | 62 | 62 | 62 | | | | | | | | | | |
| E2 | | | | | | | | | | 62 | 62 | 62 | | | | | | | |
| F1 | | | | | | | | | | | | | 62 | 62 | 62 | | | | |
| F2 | | | | | | | | | | | | | | | | 62 | 62 | 62 | 100 |
| X | 8 | | | 8 | | | 8 | | | 8 | | | 8 | | | 8 | | | |
| Y | | 8 | | | 8 | | | 8 | | | 8 | | | 8 | | | 8 | | |
| Z | | | 8 | | | 8 | | | 8 | | | 8 | | | 8 | | | 8 | |
| WATER | 30 | 30 | 30 | 30 | 30 | 30 | 30 | 30 | 30 | 30 | 30 | 30 | 30 | 30 | 30 | 30 | 30 | 30 | |
| TOTAL | 100 | 100 | 100 | 100 | 100 | 100 | 100 | 100 | 100 | 100 | 100 | 100 | 100 | 100 | 100 | 100 | 100 | 100 | 100 |

TABLE 4

The organic surfactant compositions were prepared by the following method:

| Surfactant system | | Parts | Parts | Parts |
|---|---|---|---|---|
| Nonionic | Lauryl ether polyoxyethylene (4) | 39 | | |
| | Lauryl ether polyoxyethylene (23) | 61 | | |
| Cationic | N-(Chloroallyl)hexamonium chloride | | 45 | |
| | Dicocodimethylammoniumchloride | | 55 | |
| Anionic | Cithrol-DGMA | | | 55 |
| | Sodium laureth 7 Sulfate | | | 45 |
| | | 100 | 100 | 100 |

For the sample with filler, Example 37, the water was omitted. Instead, 400 grams of soap powder/talc/treated silica filler was added to the surfactant blend before mixing with the silicone component. This resulted in a granular material, which was easily incorporated in a soap bar.

In order to demonstrate the improved surface deposition of the compositions including the cationised silicone delivery system of the invention of the present invention, the controls were compared to soap bars made with various silicone blends and with the compositions of the present invention. The soaps were evaluated for skin feel and the relative amount of silicone deposited by each composition, termed % retention, was determined.

Percent retention was determined by quantitative IR analysis using a Nicolette FTIR spectrometer. The procedure for standardisation and analysis are based on the methodology as per the following protocol. The protocol for measuring retention is detailed hereunder.

Working standards of cyclomethicone solutions were prepared in the concentration range of 0.15 mg/g-26 mg/g. The IR spectrum of each solution was recorded. A calibration procedure was developed based on partial least mean square centering available in the equipment. The peak area under the Si—Me absorption band at 1260 nm was considered for quantification. The calibration curve was linear throughout the concentration range of the silicone solutions used. The slope and intercept of the calibration curve followed an equation for a straight line.

For each experimental composition, a solution of 1 gram soap (containing 1% of the composition) in 100 grams water was prepared. The solution was applied to a substrate (closely woven polyester) with a brush and allowed to dry for 20-30 minutes. The quantity applied was determined by the difference between the weights of the solution bottle plus the brush before and after the solution was applied. After application and drying, the site was rinsed with water and the rinse water was collected. The silicone content of the rinse water was determined (using FTIR) from the area under the peak for the Si—Me absorption at 1260 nm. The following equation was used for the calculation of % retention:

% Retention=(Silicone applied−Silicone washed off)
*100/Silicone applied

TABLE 3

| | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| Silicone applied, mg/g | 5 | 5 | 5 | 5 | 5 | 5 | 5 | 5 | 5 | 5 | 5 | 5 | 5 | 5 | 5 | 5 | 5 |
| Silicone washed off, mg/g | 2.5 | 6 | 6 | 2 | 2.1 | 2.3 | 2 | 2.3 | 2.3 | 2.2 | 2.1 | 2.3 | 2.1 | 2.1 | 2.1 | 2.1 | 2 |
| % Retention | 50 | 50 | 50 | 61 | 59 | 55 | 55 | 55 | 55 | 56 | 58 | 55 | 58 | 58 | 58 | 58 | 60 |

| | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|
| Silicone applied, mg/g | 5 | 5 | 5 | 5 | 5 | 5 | 5 | 5 | 5 | 5 | 5 | 5 | 5 | 5 | 5 | 5 | 5 | 5 | 5 | 5 |
| Silicone washed off, mg/g | 2 | 2 | 2 | 2 | 2 | 1.4 | 1.5 | 2 | 2 | 2 | 1.3 | 1.5 | 1.5 | 1.3 | 1 | 1 | 0.3 | 0.3 | 0.3 | |
| % Retention | 61 | 60 | 60 | 50 | 70 | 72 | 70 | 59 | 62 | 60 | 75 | 70 | 71 | 75 | 80 | 78 | 94 | 94 | 94 | 95 |

Results of the Retention Analysis appear in Table 3.

Skin feel was evaluated subjectively by applying a soap solution using a brush to a section of the forearm using a standard wash-rinse procedure of 15 soap rubs and 10 water rinses. The compositions of the invention also had improved skin feel over the controls.

It is thus possible by way of the present invention to provide for a silicon delivery system suitable for incorporation in wide range of cosmetic or other rinseoff formulations which would serve for effective delivery of the silicone for desired benefit attributes. In particular the invention provides for cationised silicones and/or cationised silicone delivery systems which would provide the desired flexibility to incorporate cationic silicones either as such or through dispersions or emulsions using nonionic, cationic and anionic surfactants in bar soap formulations.

The cationised silicones and/or cationised silicone delivery systems of the invention would provide for desired delivery and retention of the silicon actives on any biological substrate even when delivered from rinseoff formulations. Importantly, the cationised silicones and/or cationised silicone delivery systems can be used as such or as an emulsion or dispersion and added to soap noodles or converted to a granular additive with conventional fillers and added directly to soap during amalgamation.

The invention claimed is:

1. A cleansing cosmetic composition comprising;
   i) a cationised silicone delivery system comprising (a) a cationised fatty alkyl silicone copolymer wherein the fatty acid moiety is a straight chain of 10-30 carbon atoms and the alkyl moiety is a straight or branched chain of 10-80 carbon atoms; (b) a cationised dimethiconol complex and (c) a cationised high viscosity lower alkyl silicone fluid selected from polyalkylsilicones, polyarylsilicones and/or polyalkylaryl silicones of viscosity in the range $0.5 \times 10^6$ centipoise and optionally (d) cationised silicone gum blend; and
   ii) detergent active.

2. The cleansing cosmetic composition of claim 1 comprising;
   i) 0.1%-20% by wt. of a selective cationised silicone delivery system comprising (a) a cationised fatty alkyl silicone copolymer wherein the fatty acid moiety is a straight chain of 10-30 carbon atoms and the alkyl moiety is a straight or branched chain of 10-80 carbon atoms; (b) cationised dimethiconol complex and (c) cationised high viscosity lower alkylsilicone fluid selected from polyalkylsilicones, polyarylsilicones and/or polyalkylarylsilicones of viscosity in the range $0.5 \times 10^6$ to $600 \times 10^6$ centipoise and optionally (d) cationised silicone gum blend;
   ii) 20%-85% by wt. detergent active; and
   iii) 0.001% 10% by wt. cationic polymer.

3. The cleaning composition of claim 1 wherein the cationised fatty alkyl silicone polymer has a viscosity of $1 \times 10^5$ to $1 \times 10^6$ cp.

4. The cleaning composition of claim 1 wherein the cationised dimethiconol complex has a viscosity of $1 \times 10^6$ to $50 \times 10^6$ cp.

5. The cleansing cosmetic composition of claim 1 wherein the cationised silicone delivery system further comprises an organic surfactant.

6. The cleansing cosmetic composition of claim 1 wherein the cationised silicone delivery system comprises;
   a) 15-50 parts of a cationised fatty alkyl silicone copolymer wherein the fatty acid moiety is a straight chain of 10-30 carbon atoms and the alkyl moiety is a straight or branched chain of 10-80 carbon atoms;
   b) 5-50 parts of a cationised dimethiconol complex;
   c) 1-50 parts of a cationised high viscosity lower alkyl silicone fluid selected from polyalkylsilicones, polyarylsilicones and/or polyalkylarylsilicones of viscosity in the range $0.5 \times 10^6$ to $600 \times 10^6$ centipoise and/optionally
   d) cationised silicone gum blend.

7. The cleaning composition of claim 6 wherein the 1 to 50 parts cationised high viscosity lower alkyl silicone fluid is with the cationised silicone gum blend.

8. The cleansing cosmetic composition of claim 1 wherein the detergent active is anionic.

9. The cleansing cosmetic composition of claim 8 wherein the anionic detergent active is soap, preferably the alkali metal salt of a carboxylic acid.

10. The cleansing composition of any of claim 1, wherein the cationised fatty alkyl silicone copolymer comprises 10 to 30 parts by weight per 100 parts of a soap additive composition.

11. The cleansing composition of claim 1, wherein the cationised dimethconol complex comprises 5 to 30 parts by weight per 100 parts of a soap additive composition.

12. The cleansing composition of claim 1, wherein the cationised high viscosity silicone fluid comprises 1 to 50 parts by weight per 100 parts of a soap additive composition.

13. The cleansing composition of any of claim 1 wherein the composition additionally comprises 0.01% to 5% of a 1:1 mixture of quaternary catalyst and dimethylsulphate.

14. The cleansing composition of claim 13 wherein the quaternary catalyst is selected from tetramethyl ammonium hydroxide, trimethyl N-propyl hydroxide and trimethyl N-2 pentyl hydroxide.

15. A method of cosmetically treating the skin or hair comprising contacting the substrate to be treated with the cleansing composition of claim 1.

16. A cosmetic cationised silicone delivery system comprising:
 a) 15-50 parts of a cationised fatty alkyl silicone copolymer wherein the fatty acid moiety is a straight chain of 10-30 carbon atoms and the alkyl moiety is a straight or branched chain of 10-80 carbon atoms;
 b) 5-50 parts of a cationised dimethiconol complex; and
 c) 1-50 parts of a cationised high viscosity lower alkyl silicone fluid selected from polyalkylsilicones, polyarylsilicones and/or polyalkylarylsilicones of viscosity in the range $0.5 \times 10^6$ to $600 \times 10^6$ centipoise with cationised silicone gum blend.

17. The cationised silicone delivery system of claim 16 further comprising 2-10 parts of an organic surfactant.

18. The cationised silicone delivery system of claim 16 wherein the fatty alkyl silicone copolymer comprises a straight or branched alkyl chain of 10 to 80 carbon atoms and a fatty acid of 10-30 carbon atoms wherein the viscosity range for the polymer is $0.5 \times 10^5$-$5 \times 10^6$ centipoise.

19. The cationised silicone delivery system of claim 16 wherein the fatty alkyl silicone copolymer is a copolymer of stearic acid and cetearyl methicone.

20. The cationised silicone delivery system of claim 16 wherein the cationised dimethiconol complex has a viscosity range from $1 \times 10^6$-$50 \times 10^6$ centipoise.

21. The cationised silicone delivery system of claim 16 wherein the blend of silicone fluid to gum is in the range 0.1:1 to 20:1.

22. The cationised silicone delivery system of claim 16 wherein the delivery system additionally comprises 0.01% to 5% of a mixture of 1:1 of quaternary catalyst and dimethyl sulphate.

23. The cationised silicone delivery system of claim 16 wherein the delivery system is in the form of an emulsion or dispersion, or is converted to a granular additive.

24. A personal care cleansing composition comprising a cationised silicone delivery system according to claim 16.

25. A personal care cleansing composition according to claim 24 wherein the cleansing composition is a bar.

26. A personal cleansing composition according to claim 24 wherein the cationised fatty alkyl silicone copolymer comprises 10 to 30 parts by weight per 100 parts of a soap additive.

27. A personal care cleansing composition according to claim 16 wherein the cationised high viscosity silicone fluid comprises 1 to 50 parts by weight per 100 parts by weight of a soap additive.

28. A process for producing the cationised silicone delivery system of claim 1 comprising the steps of
 a) providing (a) a cationised fatty alkyl silicone copolymer wherein the fatty acid moiety is a straight chain of 10-30 carbon atoms and the alkyl moiety is a straight or branched chain of 10-80 carbon atoms; (b) a cationised dimethiconol complex and, (c) a cationised high viscosity lower alkyl silicone fluid selected from polyalkylsilicones, polyarylsilicones and/or polyalkylarylsilicones of viscosity in the range 0.5×106 to 600×106 centipoise with cationised silicone gum blend and optionally (d) a cationised silicone gum blend;
 b) mixing the actives in an inert atmosphere, with iso-propyl alcohol, using a mechanical stirrer;
 c) heating the mixture to 70° C.
 d) adding quaternizing catalyst and dimethylsulphate to the mixture and maintaining the reactor at 70° C. for 4 hours;
 e) removing the iso-propyl alcohol, washing the polymer and drying under vacuum for several hours.

\* \* \* \* \*